United States Patent
Wildes et al.

[11] Patent Number: 5,897,501
[45] Date of Patent: Apr. 27, 1999

[54] IMAGING SYSTEM WITH MULTIPLEXER FOR CONTROLLING A MULTI-ROW ULTRASONIC TRANSDUCER ARRAY

[75] Inventors: Douglas Glenn Wildes, Ballston Lake, N.Y.; Gregory Allen Lillegard, Greenfield, Wis.

[73] Assignee: General Electric Company, Schenectady, N.Y.

[21] Appl. No.: 09/026,660

[22] Filed: Feb. 20, 1998

Related U.S. Application Data

[60] Provisional application No. 60/045,891, May 7, 1997.
[51] Int. Cl.⁶ ......................................................... A61B 8/00
[52] U.S. Cl. ............................................. 600/447; 600/444
[58] Field of Search ...................................... 600/437–440, 600/449, 453, 447, 462; 128/916; 364/413.25; 73/606

[56] References Cited

U.S. PATENT DOCUMENTS

| | | | |
|---|---|---|---|
| 4,641,660 | 2/1987 | Bele | 128/660 |
| 5,027,820 | 7/1991 | Pesque | 128/660.07 |
| 5,083,568 | 1/1992 | Shimazaki et al. | 128/662.03 |
| 5,186,175 | 2/1993 | Hirama et al. | 128/661.01 |
| 5,229,933 | 7/1993 | Larson, III | 364/413.25 |
| 5,301,168 | 4/1994 | Miller | 367/138 |
| 5,329,930 | 7/1994 | Thomas, III et al. | 128/661.01 |
| 5,460,180 | 10/1995 | Klepper et al. | 600/447 |
| 5,490,512 | 2/1996 | Kwon et al. | 128/661.01 |
| 5,520,187 | 5/1996 | Snyder | 128/661.01 |
| 5,546,807 | 8/1996 | Oxaal et al. | 73/606 |
| 5,622,177 | 4/1997 | Breimesser et al. | 600/462 |
| 5,655,536 | 8/1997 | Takamizawa | 600/447 |
| 5,671,746 | 9/1997 | Dreschel et al. | 600/447 |

Primary Examiner—Marvin M. Lateef
Assistant Examiner—Ali M. Imam
Attorney, Agent, or Firm—Marvin Snyder; Douglas E. Stoner

[57] ABSTRACT

In an ultrasound imaging system, a multiplexer connects a beamformer to a multi-row transducer array, where the array has more electrically independent transducer elements than the beamformer has channels, so as to provide dynamic selection and beamforming control of multi-row apertures. The multiplexer allows the active aperture to be scanned along at least one axis of the array and allows the shape of the active aperture to be varied electronically. The multiplexer, which supports transmit and receive apertures appropriate for synthetic aperture beamforming, is of modular construction, enabling multiplexers appropriate for transducer arrays with various numbers of rows and columns of elements to be easily assembled from a standard set of parts. The multiplexer is physically designed as a passive backplane into which various switch cards can be plugged. The card connectors are arranged in two parallel columns. Traces from system channels are distributed on the backplane; coaxial leads from transducer elements are connected to the switch cards.

20 Claims, 12 Drawing Sheets

FIG. 3

| | 0 | 1 | 2 | 3 | 4 | 5 | 6 | 7 | 8 | 9 | 10 | 11,12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| A | 8 | 9 | 10 | 11 | 12 | 13 | 14 | 15 | 0 | 1 | 2 | 3,4 | 5 | 6 | 7 | 8 | 9 | 10 | 11 | 12 | 13 | 14 | 15 |
| B | 0 | 1 | 2 | 3 | 4 | 5 | 6 | 7 | 8 | 9 | 10 | 11,12 | 13 | 14 | 15 | 0 | 1 | 2 | 3 | 4 | 5 | 6 | 7 |
| C | 0 | 1 | 2 | 3 | 4 | 5 | 6 | 7 | 8 | 9 | 10 | 11,12 | 13 | 14 | 15 | 0 | 1 | 2 | 3 | 4 | 5 | 6 | 7 |
| D | 0 | 1 | 2 | 3 | 4 | 5 | 6 | 7 | 8 | 9 | 10 | 11,12 | 13 | 14 | 15 | 0 | 1 | 2 | 3 | 4 | 5 | 6 | 7 |
| E | | | | | | | | | | | | | | | | | | | | | | | |
| F | | | | | | | | | | | | | | | | | | | | | | | |
| G | | | | | | | | | | | | | | | | | | | | | | | |
| H | | | | | | | | | | | | | | | | | | | | | | | |

FIG. 7

|   | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|----|----|----|----|----|----|----|----|----|----|----|----|----|----|
| A | 4 | 5 | 6 | 7 | 8 | 9 | 10 | 11 | 12 | 13 | 14 | 15 |   |   |   |   |   |   |   |   |   |   |   |   |
|   | 20 | 21 | 22 | 23 | 24 | 25 | 26 | 27 | 28 | 29 | 30 | 31 | 0 | 1 | 2 | 3 | 4 | 5 | 6 | 7 | 8 | 9 | 10 | 11 |
| B | 28 | 29 | 30 | 31 |   |   |   |   |   |   |    |    |    |    |    |    | 16 | 17 | 18 | 19 | 20 | 21 | 18 | 19 |
|   | 12 | 13 | 14 | 15 | 16 | 17 | 18 | 19 | 20 | 21 | 22 | 23 | 24 | 25 | 26 | 27 | 28 | 29 | 30 | 31 | 0 | 1 | 2 | 3 |
| C |   |   |   |   |   |   |   |   |   |   |    |    | 0 | 1 | 2 | 3 | 4 | 5 | 6 | 7 | 8 | 9 | 10 | 11 |
|   | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
| D | 28 | 29 | 30 | 31 | 0 | 1 | 2 | 3 | 4 | 5 | 6 | 7 | 8 | 9 | 10 | 11 | 12 | 13 | 14 | 15 | 16 | 17 | 18 | 19 |
|   | 20 | 21 | 22 | 23 | 24 | 25 | 26 | 27 | 28 | 29 | 30 | 31 |   |   |   |   |   |   |   |   |   |   |   |   |
| E |   |   |   |   | 8 | 9 | 10 | 11 | 12 | 13 | 14 | 15 | 0 | 1 | 2 | 3 | 4 | 5 | 6 | 7 | 8 | 9 | 10 | 11 |
| F | 12 | 13 | 14 | 15 | 16 | 17 | 18 | 19 | 20 | 21 | 22 | 23 | 24 | 25 | 26 | 27 | 28 | 29 | 30 | 31 | 0 | 1 | 2 | 3 |
|   | 28 | 29 | 30 | 31 |   |   |   |   |   |   |    |    |    |    |    |    | 16 | 17 | 18 | 19 |   |   |   |   |

FIG. 8

|   | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|----|----|----|----|----|----|----|----|----|----|----|----|----|----|
| A | 4 | 21 | 22 | 23 | 24 | 25 | 26 | 27 | 28 | 13 | 14 | 15 |  |  |  |  |  |  |  |  |  |  |  |  |
| B | 20 |  |  |  |  |  |  |  |  | 29 | 30 | 31 | 0 | 1 | 2 | 3 | 4 | 5 | 6 | 7 | 8 | 9 | 10 | 11 |
| C | 28 | 13 | 14 | 15 | 16 | 17 | 18 | 19 | 20 | 21 | 22 | 23 | 24 | 25 | 26 | 27 | 28 | 29 | 30 | 31 | 16 | 17 | 18 | 19 |
| D | 12 | 5 | 6 | 7 | 8 | 9 | 10 | 11 | 12 | 13 | 14 | 15 |  |  |  |  | 0 | 1 | 2 | 3 |  |  |  |  |
|   | 4 | 29 | 30 | 31 | 0 | 1 | 2 | 3 | 4 | 5 | 6 | 7 | 16 | 17 | 18 | 19 | 24 | 25 | 26 | 27 | 24 | 25 | 26 | 27 |
|   | 28 |  |  |  |  |  |  |  |  | 21 | 22 | 23 | 24 | 25 | 26 |  | 8 | 9 | 10 | 11 |  |  |  |  |
| E | 20 | 21 | 22 | 23 | 24 | 25 | 26 | 27 | 28 | 29 | 30 | 31 | 0 | 1 | 2 | 3 | 4 | 5 | 6 | 7 |  |  |  |  |
|   | 4 | 5 | 6 | 7 | 8 | 9 | 10 | 11 | 12 | 13 | 14 | 15 |  |  |  |  | 8 | 9 | 10 | 11 | 0 | 1 | 2 | 3 |
| F | 12 | 13 | 14 | 15 | 16 | 17 | 18 | 19 | 20 | 21 | 22 | 23 | 24 | 25 | 26 | 27 | 28 | 29 | 30 | 31 | 16 | 17 | 18 | 19 |
|   | 28 | 29 | 30 | 31 |  |  |  |  |  |  |  |  |  |  |  |  |  |  |  |  |  |  |  |  |

IMAGING SYSTEM WITH MULTIPLEXER FOR CONTROLLING A MULTI-ROW ULTRASONIC TRANSDUCER ARRAY

CROSS REFERENCE TO RELATED APPLICATION

This application claims the benefit of US Provisional Application 60/045,891, filed May 7, 1997.

FIELD OF THE INVENTION

This invention relates to medical ultrasound imaging systems which have a multi-row ultrasound transducer array and, in particular, to such multi-row ultrasound transducer array in which the number of transducers is greater than the number of beamformer channels.

BACKGROUND OF THE INVENTION

A conventional ultrasound imaging system comprises an array of ultrasonic transducers for transmitting an ultrasound beam and receiving a reflected beam from the object being studied. For ultrasound imaging, a one-dimensional array typically has a multiplicity of transducers arranged in a line and driven with separate voltages. By selecting the time delay (or phase) and amplitude of the applied voltages, the individual transducers can be controlled to produce ultrasonic waves which combine to form a net ultrasonic wave that travels along a preferred vector direction and is focused at a selected point along the beam. Multiple firings may be used to acquire data representing the same anatomical information. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. By changing the time delay and amplitude of the applied voltages, the beam with its focal point can be moved in a plane to scan the object.

The same principles apply when the transducer array is employed to receive the reflected sound energy (receiver mode). The voltages produced at the receiving transducers are summed so that the net signal is indicative of the ultrasound reflected from a single focal point in the object. As with the transmission mode, this focused reception of the ultrasonic energy is achieved by imparting a separate time delay (and/or phase shift) and gain to the signal from each receiving transducer.

A phased-array ultrasound transducer is made up of an array of small piezoelectric transducer elements, with an independent electrical connection to each element. In most conventional transducers the elements are arranged in a single row, spaced at a fine pitch (one-half to one acoustic wavelength on center). As used herein, the term "1D" transducer array refers to a single-row transducer array having an elevation aperture which is fixed and an elevation focus which is at a fixed range. Electronic circuitry coupled to the elements uses time delays, and sometimes phase rotations, to control the transmitted and received signals and form ultrasound beams which are steered and focused throughout the imaging plane. For some ultrasound systems and probes, the number of transducer elements in the probe exceeds the number of channels of beamformer electronics in the system. In these cases an electronic multiplexer is used to dynamically couple the available channels to different (typically contiguous) subsets of the transducer elements during different portions of the image formation process.

A typical 1D linear or convex transducer array and multiplexer may operate with 128 beamformer channels, but the transducer array itself may have significantly more elements. A multiplexer can allow a set of contiguous transducer elements to be simultaneously coupled to the beamformer channels via coaxial cables. By closing switches coupled to respective transducer elements in a set, the beamformer may be coupled to one end of the transducer array and focused beams of ultrasound may be transmitted and received to acquire data for the corresponding edge of the image. As the point of origin of successive ultrasound beams steps along the transducer array toward the opposite end, it becomes advantageous to shift the active aperture so that the origin of the ultrasound beam is centered within it. To shift the aperture from the extreme left end of the array, for example, by one element toward the opposite end, the multiplexer switch coupled to the first element is opened and the switch coupled to the last element in a subsequent set is closed. This shifts the first beamformer channel from the one end to the opposite end of the active aperture, while leaving all other channels and elements connected as before. The time delays and other beamforming parameters are changed by the software to correspond to the new multiplexer state and one or more additional image vectors are acquired. Then the aperture is stepped further to the right, by opening the switch coupled to the second element and closing the switch coupled to the next element in the subsequent set. In this manner the active aperture can be stepped sequentially from one end of the transducer array to the other.

Various types of multi-row transducer arrays, including so-called "1.25D", "1.5D", "1.75D" and "2D" arrays, have been developed to improve upon the limited elevation performance of 1D arrays. As used herein, these terms have the following meanings: 1.25D) elevation aperture is variable, but focusing remains static; 1.5D) elevation aperture, shading, and focusing are dynamically variable, but symmetric about the centerline of the array; 1.75D) elevation geometry and control are similar to 1.5D, but without the symmetry constraint; and 2D) elevation geometry and performance are comparable to azimuth, with full electronic apodization, focusing and steering. The elevation aperture of a 1.25D probe increases with range, but the elevation focusing of that aperture is static and determined principally by a mechanical lens, with a fixed focus (or fixed foci). 1.25D probes can provide substantially better near-field and far-field slice thickness performance than 1D probes, and require no additional system beamformer channels. 1.5D probes use additional beamformer channels to provide dynamic focusing and apodization in elevation. 1.5D probes can provide detail resolution comparable to, and contrast resolution substantially better than, 1.25D probes, particularly in the mid-field and far-field. 1.75D probes, with independent control of the beamforming time delays for all elements in the aperture, allow the beamformer to adaptively compensate for inhomogeneous propagation velocities in the body (or nonuniformities in the imaging system or transducer). In addition to such adaptive beamforming or phase aberration control, 1.75D probes may also support limited beam steering in the elevation direction.

By providing at least apodization (1.25D) and perhaps dynamic beamforming (1.5D), phase aberration control (1.75D), or full 2D beam steering, multi-row transducer arrays significantly improve upon the limited elevation performance of 1D probes. However, as the number of elements in the transducer increases, the number of channels in the beamformer is not keeping pace, and the function of the multiplexer is increasingly important.

U.S. Pat. No. 5,520,187 to Snyder, the disclosure of which is incorporated by reference herein, while not discussing multi-row transducer arrays, describes a flexible multiplexer which supports different multiplexer states for systems with different numbers of beamformer channels. The multiplexer states can be reprogrammed by the ultrasound imaging system, e.g., via a serial interface. These features are advantageously used in multi-row array multiplexers such as those disclosed hereinbelow.

U.S. Pat. No. 5,329,930 to Thomas and Harsh, the disclosure of which is incorporated by reference herein, discloses a method of synthetic aperture imaging, whereby a finite number of system beamformer channels are coupled via a multiplexer to successive subsets of a large number of transducer elements. For each desired image vector and for each subset of the transducer elements, an acoustic beam is transmitted, received and summed coherently with the acoustic data from the other subsets of the transducer elements. In this way an N-channel beamformer can achieve most of the resolution and signal-to-noise performance available from an (M×N)-element transducer, albeit at the cost of M transmit-receive cycles per resulting image vector (hence the name 1-for-M or 1:M imaging). Thomas and Harsh discuss criteria for the multiplexer but do not disclose any specific design for it. The multiplexer disclosed hereinbelow satisfies the criteria of U.S. Pat. No. 5,329,930 and is designed to support 1:M beamforming of 1.5D and 1.75D transducer arrays.

SUMMARY OF THE INVENTION

A beamformer is coupled through a multiplexer to a multi-row array transducer having more electrically independent elements than the beamformer has channels, in order to provide dynamic selection and beamforming control of multi-row apertures. The multiplexer allows the active aperture to be scanned along at least one axis of the array and allows the shape of the active aperture to be varied electronically. The multiplexer supports transmit and receive apertures appropriate for synthetic aperture beamforming. In addition, the multiplexer contains relatively few switches, resulting in economy of cost and size. To minimize signal attenuation, the multiplexer is designed to never impose two or more switches in series along any signal path between a beamformer channel and a transducer element. In accordance with a preferred embodiment, the multiplexer is of modular construction. This feature facilitates easy assembly of multiplexers appropriate for transducer arrays with different numbers of rows and columns of elements, from a standard set of parts.

In particular, the multiplexer for a multi-row transducer array is designed so that the connections between system channels and transducer elements obey the following design rules:

Rule I. The order and cycle length of the channel to element assignments is the same for all rows.

Rule II. The rows of the aperture are grouped in pairs. Channel assignments in one row of each pair are offset from the assignments in the other row by one-half the cycle length.

Rule III. Pairs of rows may also be grouped in quads. Channel assignments in one pair of each quad are offset from the assignments in the other pair by one-quarter of the cycle length.

Rule IV. If any element is connected through switches to two channels, then the two channels connected to that element are one-half the cycle length apart.

The physical design of the multiplexer is that of a passive backplane into which various switch cards can be plugged. The card connectors are arranged in two parallel columns. Traces from system channels are distributed on the backplane; coaxial leads from transducer elements are connected to the switch cards. The arrangement of system channel traces on the backplane is such that Rule IV can be satisfied by double-width switch cards which plug into both halves of the back-plane.

BRIEF DESCRIPTION OF THE DRAWINGS

FIG. 3 is a schematic showing of an 8-row by 24-column transducer array with electrical connections to a 16-channel beamformer for 1.25D and 1.5D imaging in accordance with a preferred embodiment of the invention.

FIG. 7 is a schematic showing of a 6-row by 24-column transducer array with electrical connections to a 32-channel beamformer for 1.25D and 1.75D imaging in accordance with another preferred embodiment of the invention.

FIG. 8 is a schematic showing of the multiplexer configuration used with the array depicted in FIG. 7 for 1.25D imaging. The active aperture is indicated by the shaded area.

FIG. 9 is a schematic showing of the multiplexer configuration used with the array depicted in FIG. 7 for 32-channel 1.75D imaging. Exemplary apertures are indicated by dark and light stippling, respectively.

FIG. 10 is a schematic showing of the multiplexer configuration used with the array depicted in FIG. 7 for 1.75D beamforming and 1:3 synthetic aperture imaging. The inner active aperture is indicated by heavy stippling; other active apertures are indicated by light stippling and cross-hatching.

DETAILED DESCRIPTION OF THE PREFERRED EMBODIMENTS

Figure 1A:
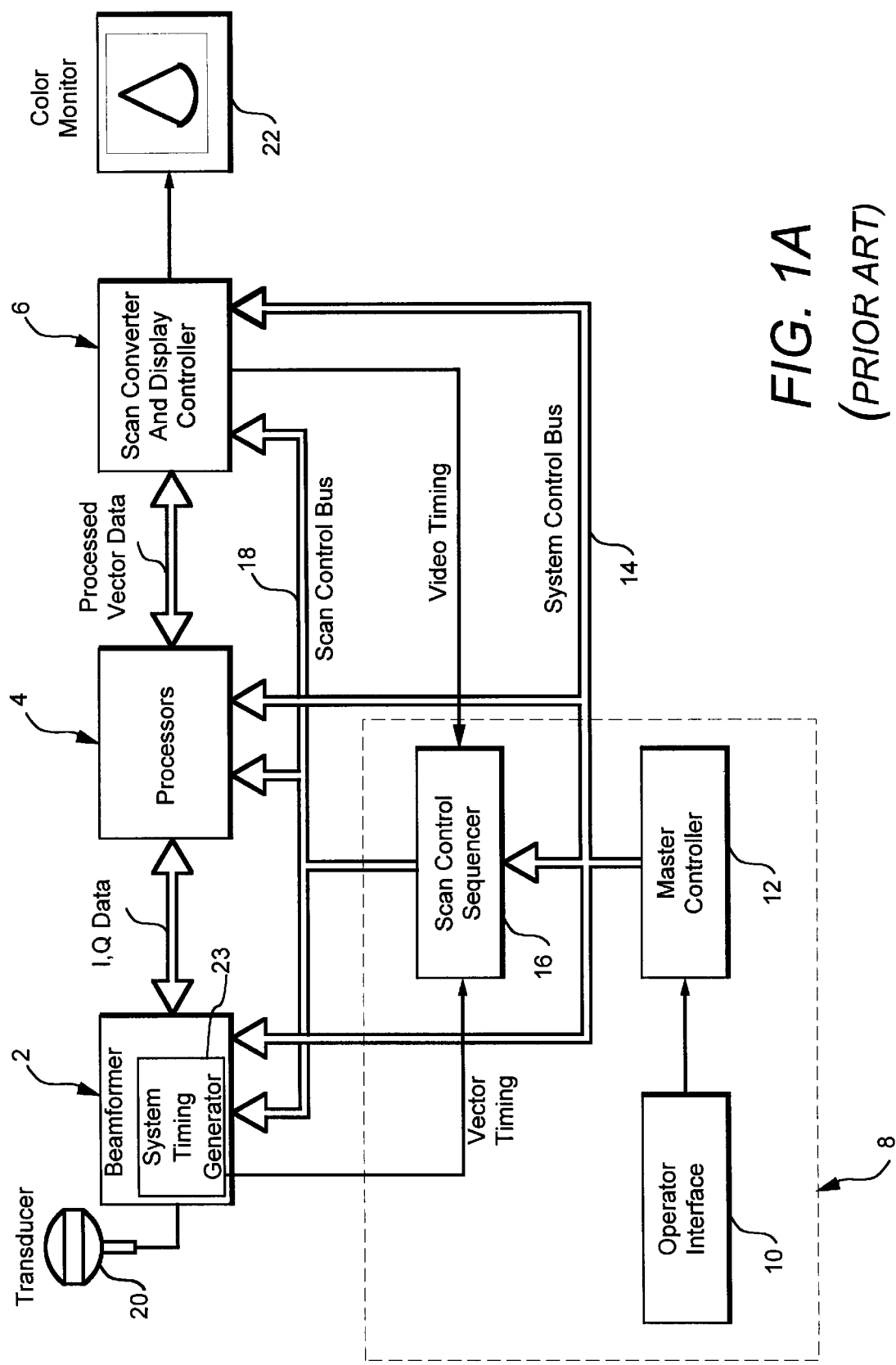
FIG. 1A is a block diagram of a conventional ultrasound imaging system.

FIG. 1A depicts an ultrasound imaging system having, as main subsystems: a beamformer 2, processors 4 (including a separate processor for each different mode), a scan converter/display controller 6 and a kernel 8. System control is centered in the kernel, which accepts operator input commands through an operator interface 10 and in turn controls the various subsystems. A master controller 12 performs system level control functions by accepting input commands from the operator via operator interface 10 as well as system status changes (e.g., mode changes), and makes appropriate system changes either directly or via a scan control sequencer 16. A system control bus 14 provides the interface from master controller 12 to the subsystems. Scan control sequencer 16 provides real-time (acoustic vector rate) control signals to beamformer 2 (including a system timing generator 23), processors 4 and scan converter 6. The scan control sequencer is programmed by its host (kernel 8) with the vector sequences and synchronization options for acoustic frame acquisitions, and broadcasts the vector parameters defined by the host to the subsystems via a scan control bus 18.

The main data path begins with analog RF (radio frequency) input signals to beamformer 2 from an ultrasonic transducer 20. Beamformer 2 supplies data to one of processors 4, where the data are processed according to the acquisition mode. The processed data are supplied as processed vector (beam) data to scan converter/display controller 6 which converts the processed vector data to video display signals for the image which are then supplied to a color monitor 22.

Figure 1B:
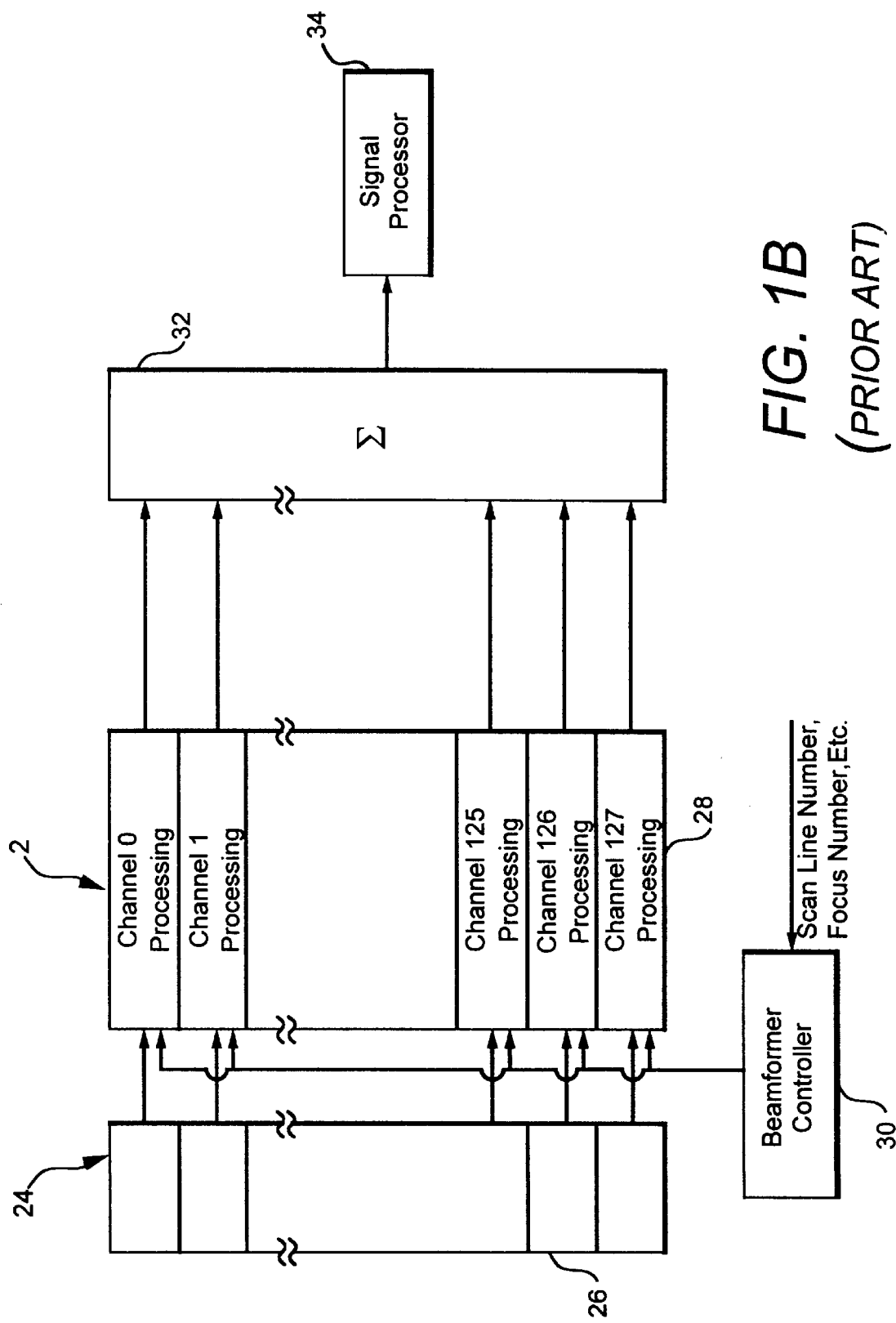
FIG. 1B is a block diagram of a typical 128-channel beamformer in a conventional ultrasound imaging system.

FIG. 1B illustrates a conventional ultrasound imaging system including a transducer array 24 comprised of a plurality of separately driven transducer elements 26, each of which, when energized by a pulsed ultrasonic waveform produced by a transmitter (not shown), produces a burst of ultrasonic energy directed at an object under study. The ultrasonic energy reflected back to transducer array 24 from the object under study is converted to an electrical signal by each receiving transducer element 26 and applied separately to beamformer 2.

The echo signals produced by each burst of ultrasonic energy reflect from objects located at successive ranges along the ultrasonic beam. The echo signals are sensed separately by each transducer element 26 and the magnitude of the echo signal at any particular instant represents the amount of reflection occurring at a specific range. Due to differences in the propagation paths between an ultrasound-scattering sample volume and each transducer element 26, however, these echo signals will not be detected simultaneously and their amplitudes will not be equal. Beamformer 2 amplifies the separate echo signals, imparts the proper time delay to each, and sums them to provide a single echo signal which accurately indicates the total ultrasonic energy reflected from the sample volume. Each beamformer channel 28 receives the analog echo signal from a respective transducer element 26.

To simultaneously sum the electrical signals produced by the echoes impinging on each transducer element 26, time delays are introduced into each separate beamformer channel 28 by a beamformer controller 30. The beam time delays for reception are the same as the time delays for transmission. However, the time delay of each beamformer channel is continuously changing during reception of the echo to provide dynamic focusing of the received beam at the range from which the echo signal emanates. The beamformer channels also have circuitry (not shown) for apodizing and filtering the received pulses.

The signals entering a summer 32 are delayed so that when they are summed with delayed signals from each of the other beamformer channels 28, the summed signals indicate the magnitude and phase of the echo signal reflected from a sample volume located along the steered beam. A signal processor or detector 34 converts the received signal to display data. In the B-mode (grey scale), the display data would be the envelope of the signal with some additional processing such as edge enhancement and logarithmic compression. The scan converter 6 (FIG. 1A) receives the display data from detector 34 and converts the data into the desired image for display. In particular, scan converter 6 converts the acoustic image data from polar coordinate (R—θ) sector format or Cartesian coordinate linear array format to appropriately scaled Cartesian coordinate display pixel data at the video rate. These scan-converted acoustic data are then supplied to display monitor 22, which displays the time-varying amplitude of the envelope of the signal as a grey scale.

Figures 2, 4:
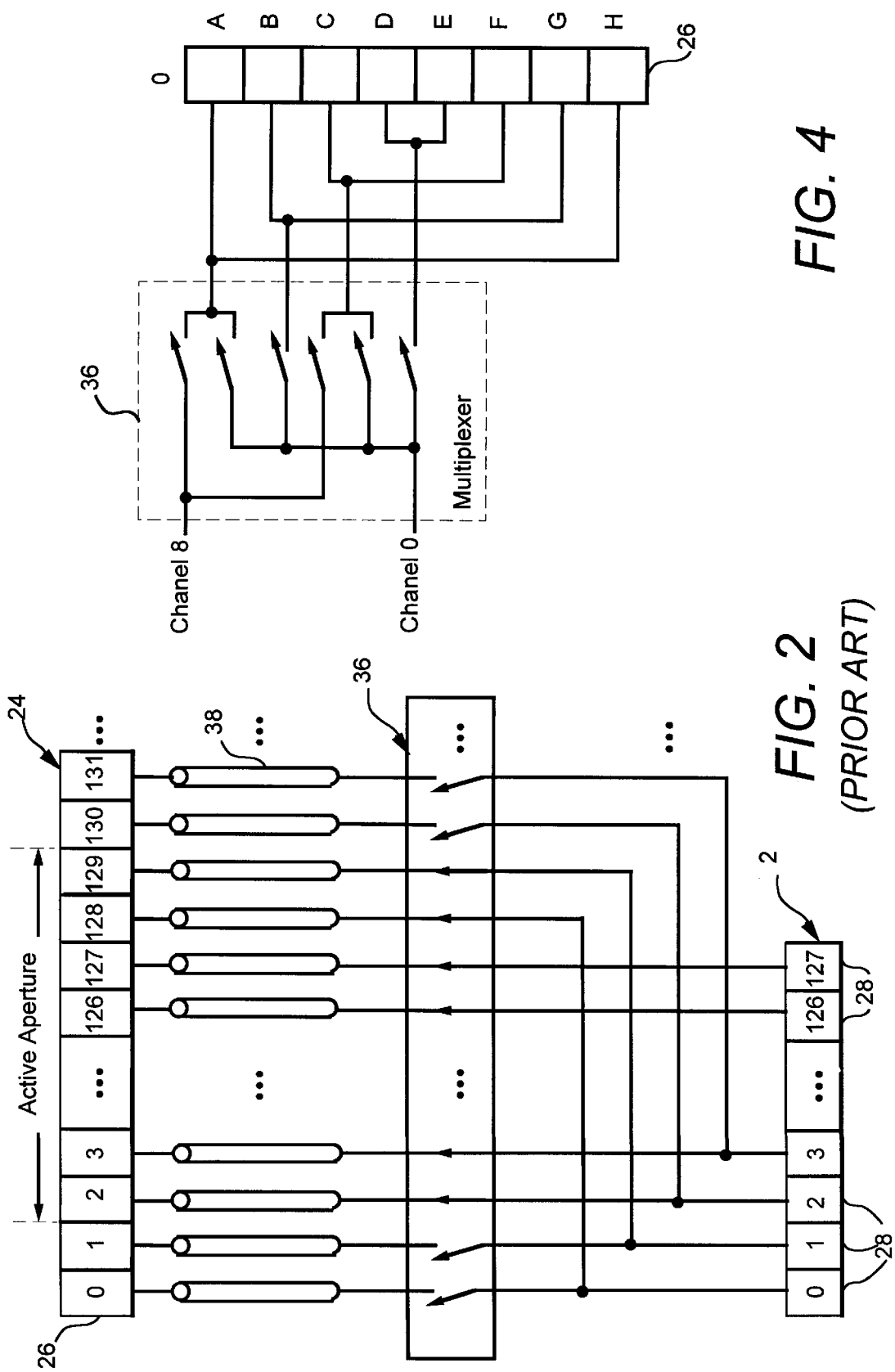
FIG. 2 is a schematic diagram of a conventional arrangement in which a multiplexer is coupled between a set of beamformer channels and a 1D transducer array having a number of elements greater than the number of beamformer channels.
FIG. 4 is a schematic illustration of electrical connections between beamformer channels 0 and 8, a multiplexer, and transducer elements A–H in column 0 of the array depicted in FIG. 3.

A typical 1D linear or convex transducer array and multiplexer is shown schematically in FIG. 2. Beamformer 2 is shown having 128 beamformer channels, but transducer array 24 has significantly more elements (typically 192 to 256). Multiplexer 36 allows any set of up to 128 contiguous transducer elements 26 to be simultaneously coupled to beamformer channels 28 via coaxial cables 38. By closing switches coupled to transducer elements 28 numbered 0 through 127, beamformer 2 is coupled to the left end of the transducer array and focused beams of ultrasound may be transmitted and received to acquire data for the corresponding edge of the image. As the point of origin of successive ultrasound beams steps along transducer array 24 to the right, it becomes advantageous to shift the active aperture so that the origin of the ultrasound beam is centered within it. To shift the aperture from the extreme left end of the array by one element toward the right, the multiplexer switch coupled to element 0 is opened and the switch coupled to element 128 is closed. This shifts beamformer channel 0 from the left end to the right side of the active aperture, while leaving all other channels and elements connected as before. The time delays and other beamforming parameters are changed by the software to correspond to the new multiplexer state and one or more additional image vectors are acquired. Then the aperture is stepped further to the right, by opening the switch coupled to element 1 and closing the switch coupled to element 129, leaving multiplexer 36 in the state shown in FIG. 2. In this manner the active aperture can be stepped sequentially from one end of the tranducer array 24 to the other. Alternatively, the same multiplexer hardware may be used to scan the active aperture more rapidly across the array by switching several transducer elements per step. In some imaging modes, successive apertures may be selected non-sequentially, jumping back and forth between the left and right ends of the transducer array.

A multiplexer for 1.25D and 1.5D beamforming with an 8-row by 24-column transducer array and a 16-channel system beamformer is illustrated in FIGS. 3–6. All apertures can be scanned across the array in the same manner as the 1D aperture and array shown in FIG. 2. The letters (A–H) and numbers (0–23) around the perimeter of FIGS. 3, 5 and 6 label the rows and columns of the array. In FIG. 3, the numbers within the matrix identify the beamformer channels (0–15) which are coupled, via multiplexer switches, to each transducer element.

FIG. 4 shows the electrical connections between beamformer channels 0 and 8, multiplexer 36, and the transducer elements in column 0 of the array depicted in FIG. 3. For 1.25D and 1.5D imaging, the eight rows of transducer elements are coupled in pairs, with each pair symmetric about the horizontal centerline of the array shown in FIG. 3.

Figure 5:
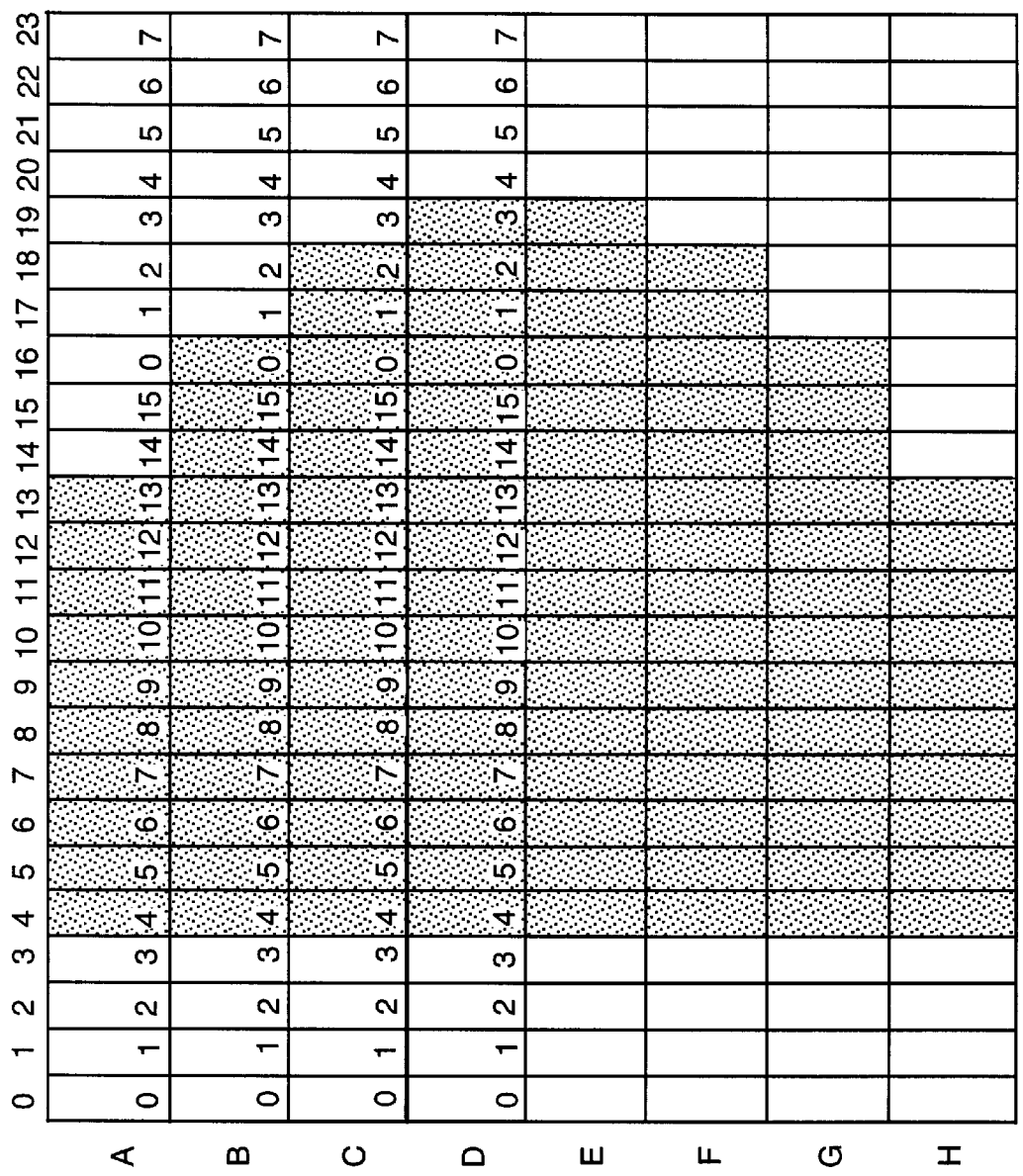
FIG. 5 is a schematic showing of the multiplexer configuration used with the array depicted in FIG. 3 for 1.25D imaging. The active aperture is indicated by the shaded area.

FIG. 5 shows the multiplexer configuration used with the array depicted in FIG. 4 for 1.25D imaging. In each column of the array, all transducer elements are coupled to the same system beamformer channel. The width of the active aperture (indicated by shading) is limited by the number of beamformer channels (e.g., 16), or may be increased M-fold if 1:M synthetic aperture imaging is used. The height of the active aperture may be as small as the central two rows or as large as the full height of the array. The shape of the aperture may be rectangular, as shown by the left side of the stippled region, or arbitrary (typically convex, approximately elliptical, as shown by the right side of the stippled region).

Figure 6:
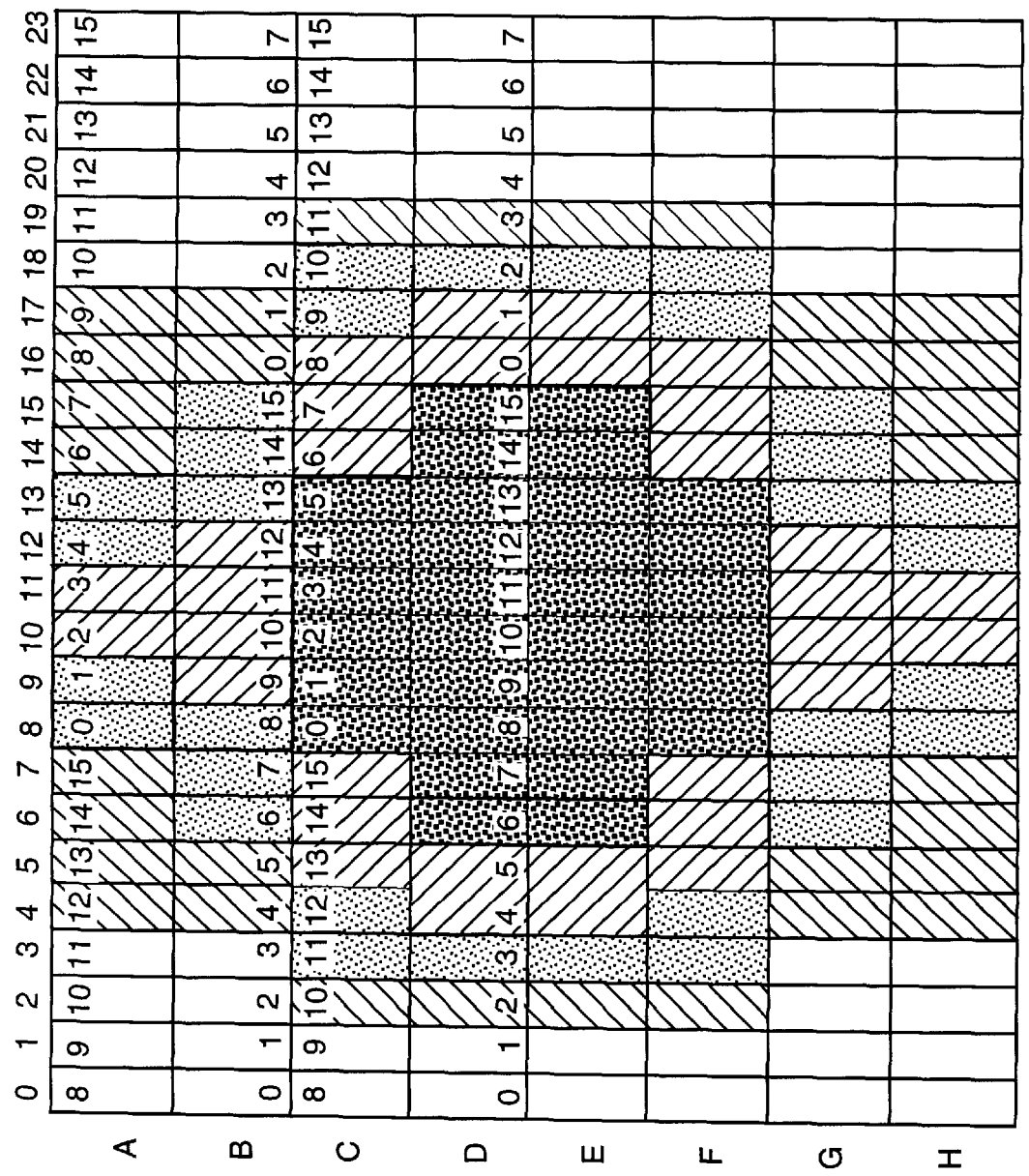
FIG. 6 is a schematic showing of the multiplexer configuration used with the array depicted in FIG. 3 for 1.5D imaging and 1:4 synthetic aperture imaging. The inner active aperture is indicated by the heavy stippling; other active apertures are indicated by light stippling and cross-hatching.

The 1.5D apertures shown in FIG. 6 are examples of the large set of aperture shapes which can be achieved with this wiring and multiplexer configuration. In particular, FIG. 6 shows the multiplexer configuration for 1.5D beamforming and 1:4 synthetic aperture imaging. The inner aperture (heavy stippling) is used alone in the near field. In the mid and far field, the surrounding apertures (\\\ hatching, light stippling, /// hatching) and 1:2 to 1:4 synthetic aperture imaging may be used to maintain a low f-number, sharp focus and high resolution.

With reference to the design rules discussed earlier, the channel-to-element assignments displayed in FIG. 3 increase from left to right in all rows. The cycle length is 16, equal to the number of system beamformer channels. In the 1.5D configuration of FIG. 6, channel assignments in rows A and C are offset from those in rows B and D by half the cycle length, i.e., 8 channels. This allows different rows to be paired when deciding the size and shape of the active apertures, e.g., the central (heavily stippled) 16-channel aperture pairs rows C and D. The shape of this aperture can be anything from 0 elements in row C and 16 in row D to 8 elements in each row (using more elements in row C than elements in row D is also possible, but would have a detrimental effect on acoustic beam quality). For the \\\-hatched 1:2 aperture, rows A and D are paired and rows B and C form a second pair. For the lighter stippled 1:3 aperture, rows A and B are paired and rows C and D are fixed at 16 elements each. Finally, for the ///-hatched 1:4 aperture, row A is paired with row C and row B with row D. These pairings, and the resulting possible 1.5D aperture shapes, are summarized in Table 1.

In Table 1, the number of system beamformer channels is represented by N. The symbols h, i, j, k, l, m represent arbitrary integers, each of which may take on any value between 0 and N/2. The numerical values associated with each symbol, for the 1.5D apertures shown in FIG. 6, are listed in the sixth column of Table 1. It will be understood that, while FIGS. 3–6 show an 8-row by 24-column transducer array and a 16-channel beamformer, the same design principles apply to 64- or 128-channel beamformers and arrays with 6, 8 or more rows and 128, 192 or more columns of elements.

TABLE 1

| FIG. 6 | Elements per Row | | | | FIG. 6 | Total Elements | Synthetic Aperture |
|---|---|---|---|---|---|---|---|
| | A + H | B + G | C + F | D + E | (N = 16) | | |
| Dark Stippling | 0 | 0 | m | N − m | m = 6 | N | |
| \\\ | k | l | N − l | N − k | k = 2, l = 4 | 2N | 1:2 |
| Light Stippling | j | N − j | N | N | j = 6 | 3N | 1:3 |
| /// | N − h | N − i | N + h | N + i | h = i = 2 | 4N | 1:4 |

For optimum performance in 1:M synthetic aperture imaging, it may be desirable to use a 1.25D aperture (FIG. 5) on transmit and a 1.5D aperture (FIG. 6) on receive. The 1.25D aperture may have less than optimal elevation beam control, but can deliver significantly greater acoustic power for penetration and signal-to-noise than a small, N-element 1.5D aperture. When receiving, 1:M synthetic aperture processing allows the full sensitivity and resolution of an M×N-element 1.5D aperture to be achieved. For this mode of operation, a multiplexer which supports both 1.25D and 1.5D operation and can switch quickly between the two configurations is essential.

A multiplexer for 1.25D and 1.75D beamforming with a 6-row by 24-column transducer array and a 32-channel system beamformer is illustrated in FIGS. 7–10. Not shown in the drawings, but also possible with the multiplexer illustrated in FIG. 7, are single-row apertures the full width of the array and three-row 1.5D apertures with up to N/2=16 elements per row. Since this array does not have hard-wired symmetry in elevation, the multiplexer is designed so that all apertures may be scanned across the array in both azimuth (horizontal) and elevation (vertical). The letters (A–H) and numbers (0–23) around the perimeter in FIG. 7 label the rows and columns of the array. The numbers within the matrix identify the beamformer channels (0–31) which are coupled, via multiplexer switches, to each transducer element. Each transducer element is independently coupled to one or two multiplexer switches. There is no constraint that the active apertures or beamforming be symmetric about the horizontal centerline of the array.

Figure 8:
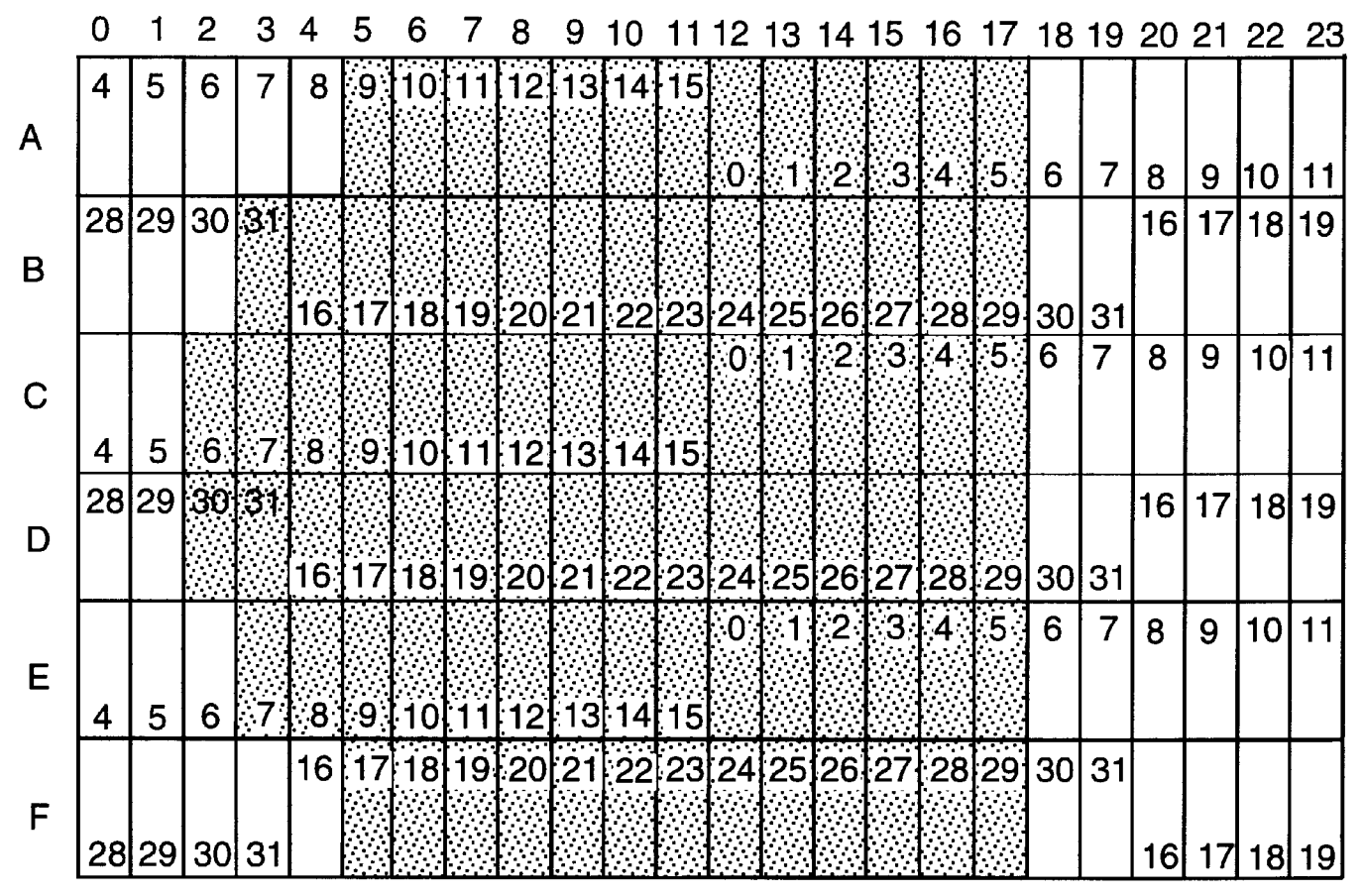

FIG. 8 shows a multiplexer configuration for 1.25D imaging. In each column of the array, all elements are connected to one or the other of a pair of system channels which are programmed with identical beamforming parameters. Because of this pairing, the maximum number of elements in any row of the active aperture (stippled) is half the number of system channels (here, N/2=16). This active width may be increased M-fold if 1:M synthetic aperture imaging is used. The height of the active aperture may be as small as one row or as large as the full height of the array. The shape of the aperture may be rectangular, as shown by the right side of the stippled region, or arbitrary (typically convex, approximately elliptical, as shown by the left side of the stippled region).

FIG. 9 shows example apertures for 32-channel 1.75D imaging. Possible apertures have m, N/2−m, N/2−l, l elements per row. In FIG. 9, N=32, m=l=8 for the heavily stippled aperture, and m=l=5 for the lightly stippled aperture. Since there is no hard-wired symmetry in elevation, all apertures may be scanned in both azimuth (horizontal) and elevation (vertical). Within each aperture, only those multiplexer switches which are closed are shown. A list of all possible channel connections for all elements is shown in FIG. 7.

Figure 10:
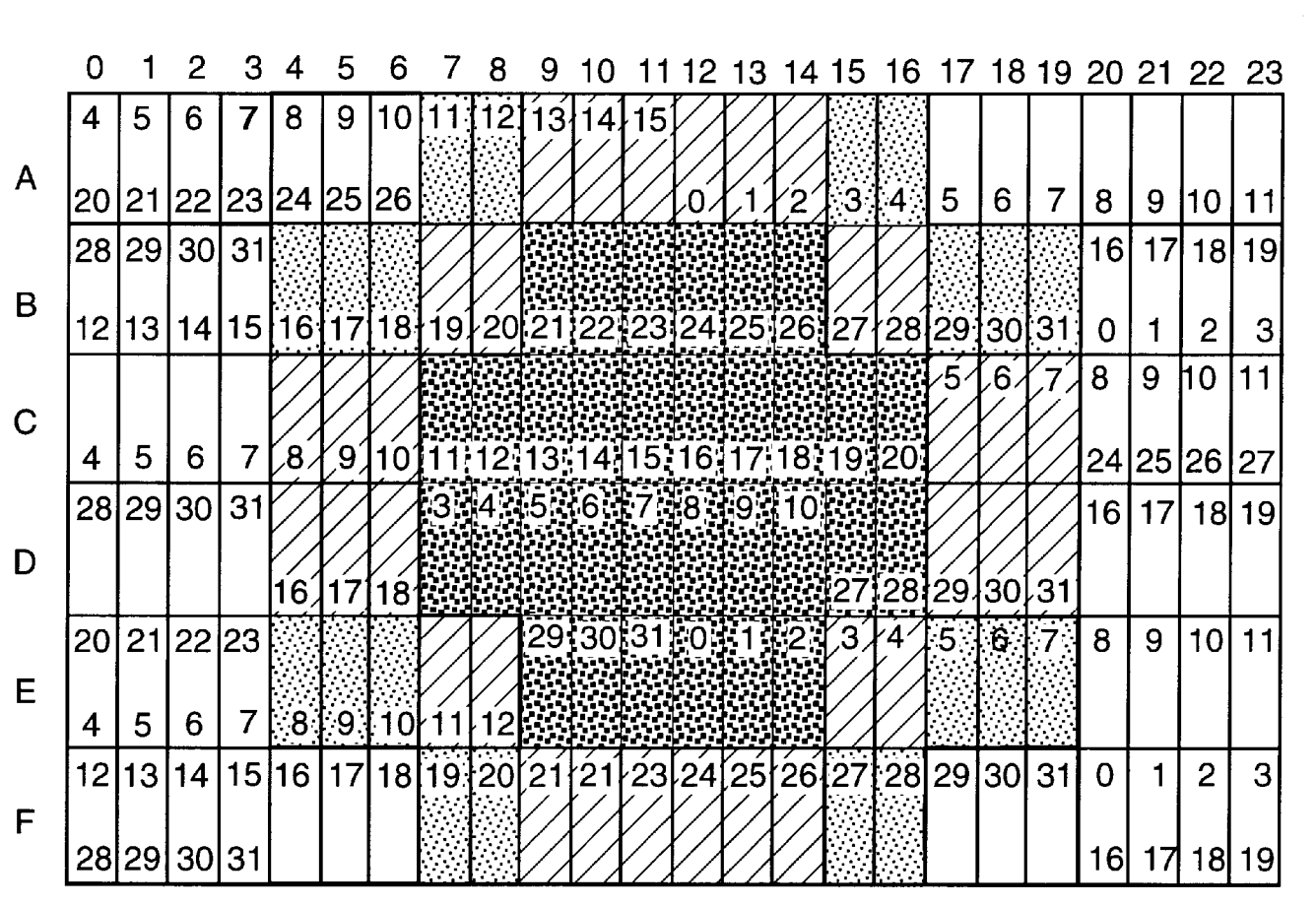

FIG. 10 shows a multiplexer configuration for 1.75D beamforming and 1:3 synthetic aperture imaging. The inner aperture (heavy stippling) is used alone in the near field. In the mid and far field, the surrounding apertures (/// hatching; light stippling) and 1:2 or 1:3 synthetic aperture imaging may be used to maintain a low f-number, sharp focus and high resolution.

With reference to the design rules, the channel-to-element assignments shown in FIG. 7 increase from left to right in all rows (Rule I). The primary cycle length is 32, equal to the number of system beamformer channels. Secondary channel connections to some of the elements in each row are offset from the primary channel connections by half the cycle length (Rule IV), allowing any of rows A, C and E to be paired together (Rule II), as well as any of rows B, D and F. Channel assignments in rows A, C and E are offset from those in rows B, D and F by one quarter of the cycle length (Rule III), allowing the creation of contiguous four-row, 32-element, 1.75D apertures which can be scanned in both azimuth and elevation (see FIG. 9).

Table 2 summarizes the 1:3 synthetic aperture 1.75D aperture shapes shown in FIG. 10. In Table 2, the number of system beamformer channels is represented by N. The symbol M represents an arbitrary integer, with value between 0 and N/2. The numerical values associated with N and m for the 1.75D apertures shown in FIG. 10 are listed in the fifth column of Table 2. Other apertures, including M×N elements for 1:M imaging with M≦4 and the entire aperture for M=5 are also possible. It will be understood that, while FIGS. 7–10 show a 6-row by 24-column transducer array and a 32-channel beamformer, the same design principles apply to 64- or 128-channel beamformers and arrays with 6, 8 or more rows and 128, 192 or more columns of elements.

TABLE 2

| FIG. | Elements per Row | | | FIG. 10 | Total Elements | Synthetic Aperture |
|---|---|---|---|---|---|---|
| 10 | A, F | B, E | C, D | (N = 32) | | |
| Dark Stippling | 0 | m | N/2 − m | m = 6 | N | |
| /// | m | N/2 − m | N/2 | | 2N | 1:2 |
| Light Stippling | N/2 − m | N/2 | N/2 | | 3N − 2m | 1:3 |

Figure 11B:
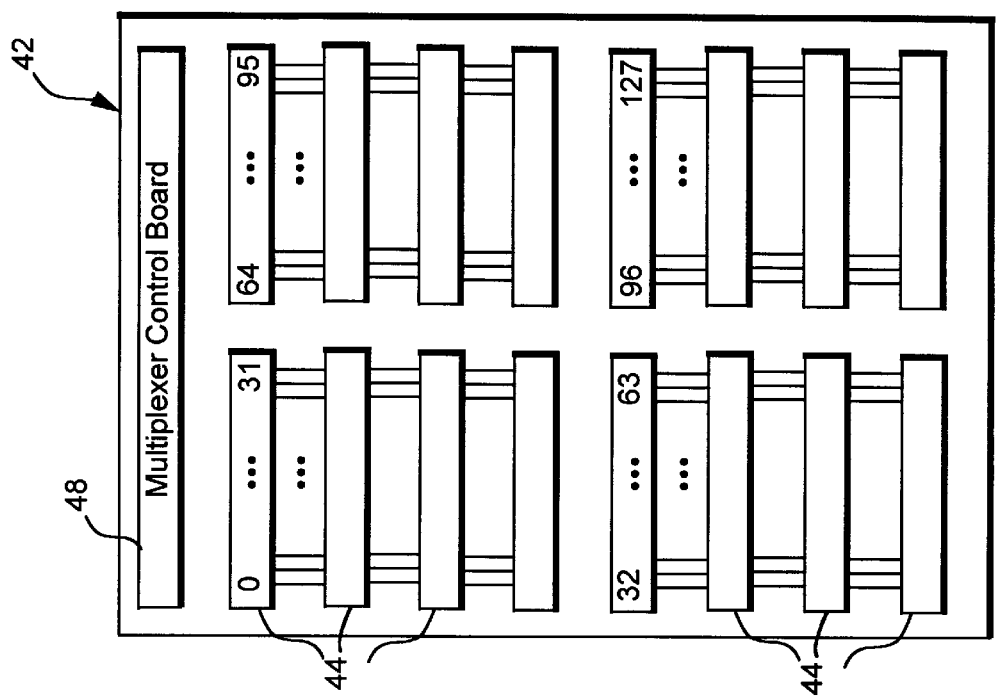
FIG. 11B is a schematic illustration of the multiplexer backplane or motherboard of the invention.
Figure 11A:
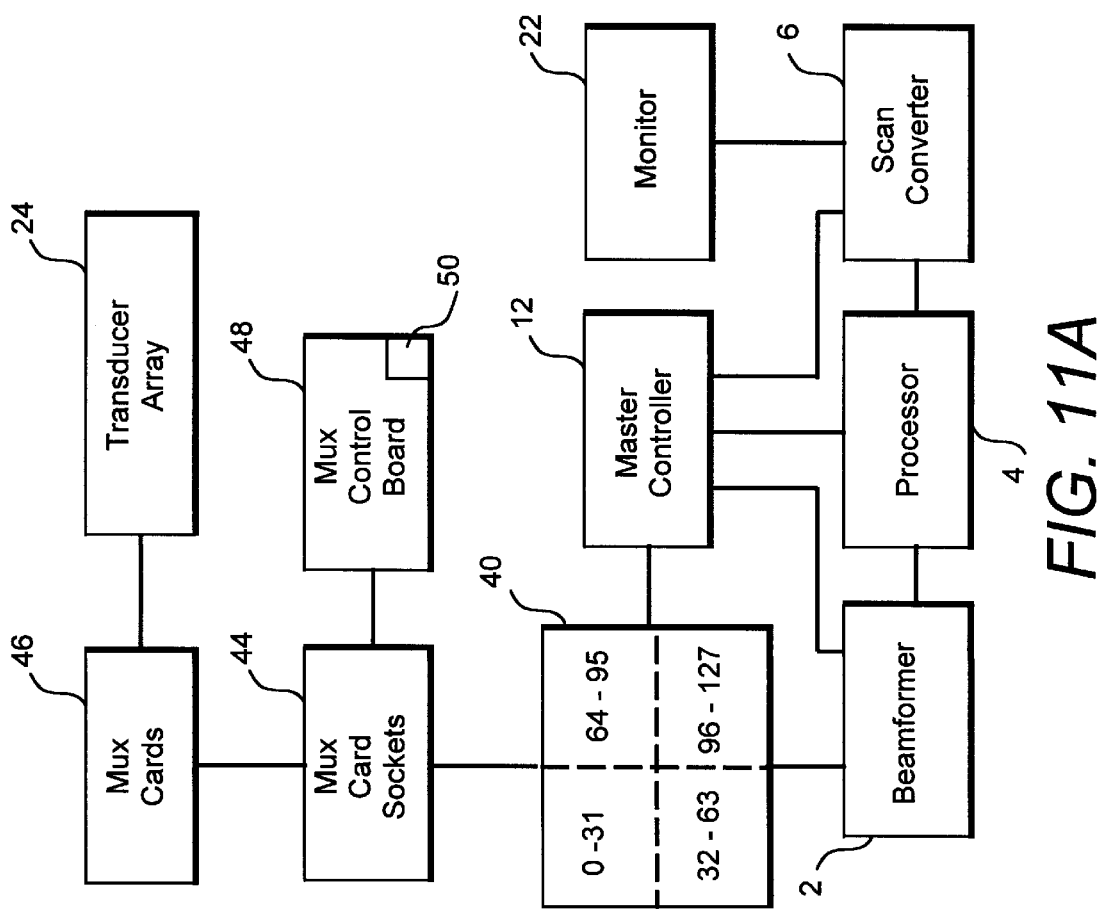
FIG. 11A is a block diagram illustrating part of an ultrasound imaging system incorporating a modular multiplexer in accordance with a preferred embodiment of the invention.

The modular hardware design which makes all of the above-described multiplexer configurations possible is shown in FIGS. 11A, 11B and 12A–12C. The configuration shown is for a 128-channel beamformer. As seen in FIG. 11A, a system console connector 40 is divided into quadrants, with connections for the 128 channels of beamformer 2 distributed among the quadrants as shown. The multiplexer is controlled by a parameter called MUX State, which is transmitted by master controller 12 to control lines on system console connector 40. The MUX State parameter is generated in accordance with a transducer multiplexer control program stored in the master controller.

The multiplexer backplane or motherboard 42, shown in FIG. 11B, mounts on system console connector 40 (FIG. 11A). Each quadrant of the backplane thus affixed to console connector 40 contains two or more (here, four) identical connectors, such as sockets 44, for multiplexer cards 46 (FIG. 11A) connected together and to the corresponding quadrant of console connector 40 in parallel. The assignment of system beamformer channels to quadrants of the console connector and multiplexer backplane and the locations of the multiplexer card sockets on the backplane are arranged so that sockets which are aligned end-to-end are coupled to beamformer channels which differ by half the multiplexer cycle length (here, by 128/2=64). The multiplexer control board 48 is coupled to control lines on the console connector and separate (not paralleled) control lines to each multiplexer card socket. Control board 48 receives a MUX State command from the master controller and uses data stored in an on-board memory 50 (ROM or EEPROM), shown in FIG. 11A to set every switch on every multiplexer card 46 to the open or closed position required for the commanded multiplexer state.

Figures 12A, 12B:
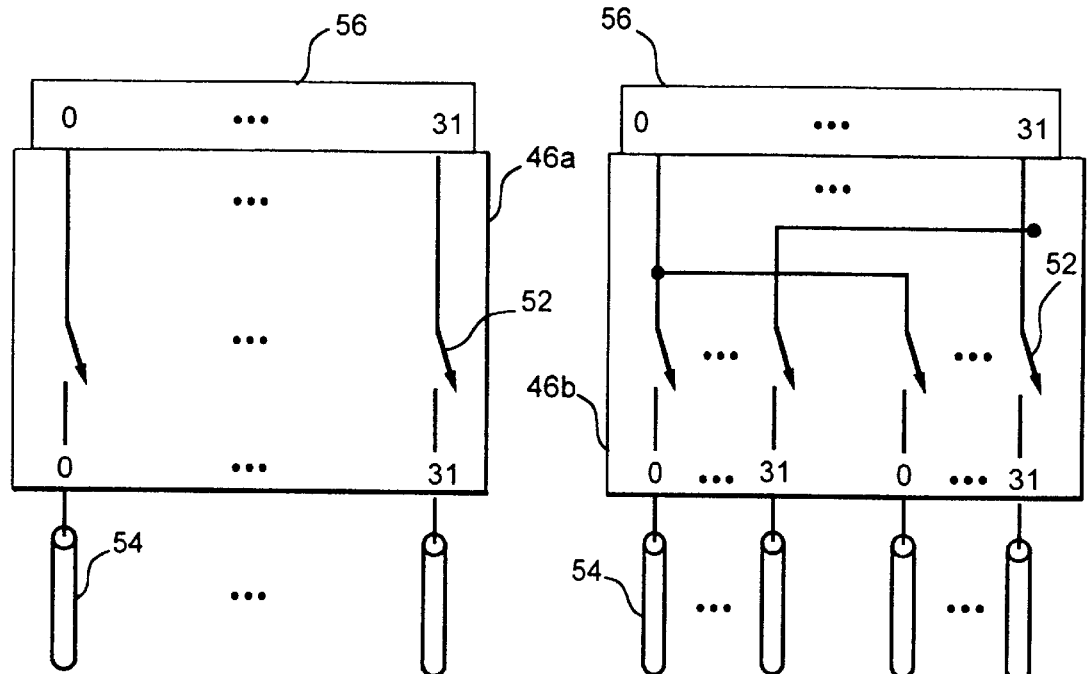
FIGS. 12A–12C are schematic illustrations showing different preferred embodiments of the multiplexer cards which plug into sockets on the multiplexer motherboard shown in FIG. 11B.
Figure 12C:
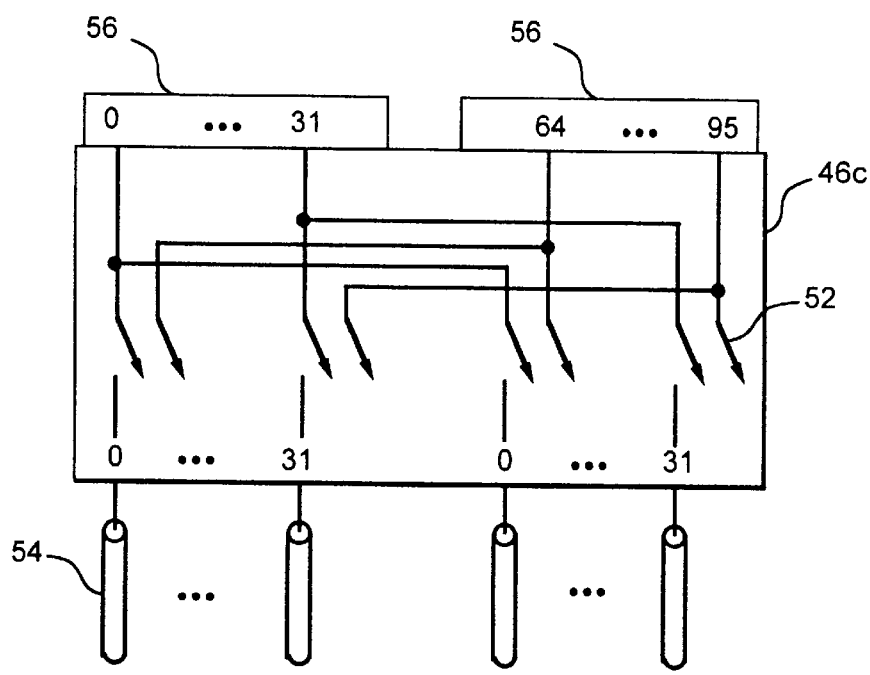

FIGS. 12A–12C show various preferred embodiments of the multiplexer cards which plug into the sockets on the multiplexer motherboard shown in FIG. 11B. Each card contains a set of individually controllable switches 52 which can connect coaxial leads 54 from transducer elements to specific system beamformer channels via a connector 56 which plugs into a socket on the multiplexer backplane. FIG. 12A shows a low-density multiplexer card 46a for connecting 32 coaxial leads to 32 system channels. FIG. 12B shows a high-density multiplexer card 46b for connecting 64 coaxial leads to 32 beamformer channels. This is equivalent to, but more compact than, two low-density 32:32 multiplexer boards plugged into adjacent sockets in the same quadrant of the multiplexer backplane. FIG. 12C shows a high-density multiplexer card 46c for connecting 64 coaxial leads to 64 system channels. Card 46c employs two connectors 56, one of which plugs into a socket in one quadrant of the motherboard and the other of which plugs into a socket of the laterally adjacent quadrant. When plugged into the multiplexer backplane, card 46c allows each coaxial lead (i.e., for each respective transducer element) connected to this card to be coupled to either of two beamformer channels which differ by half the cycle length (thus satisfying Rule IV).

The foregoing preferred embodiments have been disclosed for the purpose of illustration. Variations and modifications will be readily apparent to those skilled in the pertinent arts. All such variations and modifications are intended to be encompassed by the claims set forth hereinafter.

We claim:

1. An ultrasound imaging system comprising:

a transducer array including first and second rows of transducer elements, each of said first and second rows comprising a respective multiplicity of said transducer elements;

a beamformer including a predetermined number of beamformer channels to form a cycle length;

switching means for multiplexing imaging data between said transducer elements of said first and second rows and said beamformer channels; and control means for selectively configuring said switching means in response to receipt of a multiplexer state command so as to establish beamformer channel to transducer element assignments;

wherein the order and cycle length of the beamformer channel to transducer element assignments is the same for said first and second rows, and a first set of channel assignments in said first row is offset from a first set of channel assignments in said second row by one-half the cycle length.

2. The ultrasound imaging system of claim 1 wherein a second set of beamformer channel to transducer element assignments for said first row is offset from said first set of beamformer channel to transducer element assignments for said first row by one-half the cycle length.

3. The ultrasound imaging system of claim 1 wherein said switching means comprises first and second switches, and wherein a first transducer element of said first row of transducer elements is selectively coupled through said first and second switches to first and second beamformer channels respectively, said first and second beamformer channels being one-half the cycle length apart.

4. The ultrasound imaging system of claim 1 wherein said transducer array further comprises third and fourth rows of transducer elements, each of said third and fourth rows including a respective multiplicity of said transducer elements, and further comprising switching means for multiplexing imaging data between said transducer elements of said third and fourth rows and said beamformer channels, wherein the order and cycle length of the beamformer channel to transducer element assignments is the same for said first through fourth rows, and a first set of channel assignments in said first row is offset from respective first sets of channel assignments in said third and fourth rows by one-quarter and three-quarters of the cycle length, respectively.

5. The ultrasound imaging system of claim 4 wherein said switching means comprises first and second switches, and wherein a first transducer element of said first row of transducer elements is selectively coupled through said first and second switches to first and second beamformer channels respectively, said first and second beamformer channels being one-half the cycle length apart.

6. The ultrasound imaging system of claim 1, further comprising a multiplexer backplane including a first connector having a multiplicity of electrical connections to a first set of beamformer channels of said multiplicity of beamformer channels and a second connector having a multiplicity of electrical connections to a second set of beamformer channels of said multiplicity of beamformer channels, said first and second sets of beamformer channels being mutually exclusive, wherein said switching means comprises first and second multiplexer cards respectively connected to said first and second connectors, said first multiplexer card comprising a first set of switches independently controllable to couple said first row of transducer elements to said first set of beamformer channels and said second multiplexer card comprising a second set of switches independently controllable to couple said second row of transducer elements to said second set of beamformer channels.

7. The ultrasound imaging system of claim 2, further comprising a multiplexer backplane including a first connector having a multiplicity of electrical connections to a first set of beamformer channels of said multiplicity of beamformer channels and a second connector having a multiplicity of electrical connections to a second set of beamformer channels of said multiplicity of beamformer channels, said first and second sets of beamformer channels being mutually exclusive and said first and second connectors being arranged end-to-end, wherein said switching means comprises a double-width multiplexer card having a first portion connected to said first connector and a second portion connected to said second connector, said multiplexer card comprising a first set of switches independently controllable to couple said first row of transducer elements to said first set of beamformer channels and a second set of switches independently controllable to couple said first row of transducer elements to said second set of beamformer channels.

8. The ultrasound imaging system of claim 6 wherein said control means comprises a multiplexer control board affixed to said multiplexer backplane and control lines for coupling said multiplexer control board to said first and second multiplexer cards for controlling the state of said first and second sets of switches.

9. The ultrasound imaging system of claim 7 wherein said control means comprises a multiplexer control board affixed to said multiplexer backplane and control lines for coupling said multiplexer control board to said multiplexer card for controlling the state of said first and second sets of switches.

10. The ultrasound imaging system of claim 6 wherein said multiplexer backplane further includes a third connector having a multiplicity of electrical connections to a third set of beamformer channels of said multiplicity of beamformer channels and a fourth connector having a multiplicity of electrical connections to a fourth set of beamformer channels of said multiplicity of beamformer channels, said first, second, third and fourth sets of beamformer channels being mutually exclusive, said switching means further comprising third and fourth multiplexer cards respectively connected to said third and fourth connectors, said third multiplexer card comprising a third set of switches independently controllable to couple a third row of transducer elements to said third set of beamformer channels and said fourth multiplexer card comprising a fourth set of switches independently controllable to couple a fourth row of transducer elements to said fourth set of beamformer channels.

11. The ultrasound imaging system of claim 1, further comprising a multiplexer backplane having four quadrants, each of said quadrants comprising a first connector having a first multiplicity of electrical connections and a second connector having a second multiplicity of electrical connections, said first and second multiplicities of electrical connections of each quadrant being coupled in parallel to a respective mutually exclusive set of beamformer channels.

12. A method for operating an ultrasound imaging system having a predetermined number of beamformer channels and a two-row array of transducer elements, comprising the steps of:

assigning each transducer element of said two rows to a respective one of said beamformer channels, each beamformer channel to transducer element assignment being provided by a respective connection including a switch selectively controllable to be open or closed, wherein the order and cycle length of the beamformer channel to transducer element assignments is the same for each of said two rows, and a first set of beamformer channel to transducer element assignments for a first of said rows is offset from a first set of beamformer channel to transducer element assignments for the second of said rows by one-half the cycle length; and selectively closing a number of switches equal to the number of beamformer channels, the switches being selected so that each beamformer channel has a respective transducer element electrically coupled thereto.

13. The method of claim 12 including the additional step of assigning at least several transducer elements of said two rows to second respective ones of said beamformer channels, wherein each second assignment of a beamformer channel to a transducer element for said first row is offset from the first assignment of a beamformer channel to said transducer element for said first row by one-half the cycle length.

14. The method of claim 12 including the additional step of assigning a first transducer element of said first row to first and second ones of said beamforming channels, said first and second ones of said beamforming channels being one-half the cycle length apart.

15. The method of claim 12, wherein said transducer array further comprises third and fourth rows of transducer elements, said method further comprising the steps of assigning each transducer element of said third and fourth rows to a respective one of said beamformer channels, each beamformer channel to third and fourth row transducer element assignment being provided by a respective connection including a switch selectively controllable to be open or closed, wherein the order and cycle length of the beamformer channel to third and fourth transducer element assignments is the same for each of the first, second, third and fourth rows, and a first set of beamformer channel to transducer element assignments in said first row is offset from respective first sets of beamformer channel assignments for said third and fourth rows by one-quarter of the cycle length and three-quarters of the cycle length, respectively.

16. The method of claim 15 including the additional step of assigning a first transducer element of said first row to first and second ones of said beamformer channels, said first and second ones of said beamformer channels being one-half the cycle length apart.

17. A multiplexer motherboard comprising first, second, third and fourth quadrants, each of said quadrants including a first socket having a first multiplicity of electrical connections and a second socket having a second multiplicity of electrical connections, said first and second multiplicities of electrical connections for each quadrant being made in parallel to a respective one of four sets of channels, said first and second sockets of said first quadrant being respectively aligned with said first and second sockets of said third quadrant, and said first and second sockets of said second quadrant being respectively aligned with said first and second sockets of said fourth quadrant.

18. The multiplexer motherboard of claim 17, further comprising first and second multiplexer cards respectively plugged into the first and second sockets of said first quadrant.

19. The multiplexer motherboard of claim 17, further comprising a double-width multiplexer card having a first portion plugged into the first socket of said first quadrant and a second portion plugged into the first socket of said third quadrant.

20. The multiplexer motherboard of claim 17, further comprising:

a multiplexer card plugged into the first socket of said first quadrant, said multiplexer card having a multiplicity of selectively controllable switches thereon;

a multiplexer control board; and circuitry for coupling said multiplexer control board to said multiplexer card via said first socket of said first quadrant for controlling the state of said switches on said multiplexer card.

* * * * *